US011869655B2

(12) United States Patent
Kamiyama

(10) Patent No.: US 11,869,655 B2
(45) Date of Patent: Jan. 9, 2024

(54) INFORMATION PROCESSING SYSTEM, ENDOSCOPE SYSTEM, INFORMATION STORAGE MEDIUM, AND INFORMATION PROCESSING METHOD

(71) Applicant: OLYMPUS CORPORATION, Hachioji (JP)

(72) Inventor: Toshiya Kamiyama, Tama (JP)

(73) Assignee: OLYMPUS CORPORATION, Hachioji (JP)

( * ) Notice: Subject to any disclaimer, the term of this patent is extended or adjusted under 35 U.S.C. 154(b) by 409 days.

(21) Appl. No.: 17/321,893

(22) Filed: May 17, 2021

(65) Prior Publication Data
US 2021/0272284 A1 Sep. 2, 2021

Related U.S. Application Data

(63) Continuation of application No. PCT/JP2019/013605, filed on Mar. 28, 2019.

(51) Int. Cl.
*G16H 30/40* (2018.01)
*G06N 3/08* (2023.01)
(Continued)

(52) U.S. Cl.
CPC ....... *G16H 30/40* (2018.01); *A61B 1/000096* (2022.02); *G06F 18/214* (2023.01);
(Continued)

(58) Field of Classification Search
CPC . G06T 2207/20081; G06T 2207/20084; G06T 7/0012; G06T 2207/30004;
(Continued)

(56) References Cited

U.S. PATENT DOCUMENTS

2005/0280809 A1 12/2005 Hidai et al.
2014/0247977 A1 9/2014 Han
(Continued)

FOREIGN PATENT DOCUMENTS

JP 2005-157679 A 6/2005
JP 2011-192178 A 9/2011
(Continued)

OTHER PUBLICATIONS

Xiaofei et al. ("Articulated Multi-Instrument 2-D Pose Estimation Using Fully Convolutional Networks") (Year: 2018).*
(Continued)

*Primary Examiner* — Dung Hong
(74) *Attorney, Agent, or Firm* — WHDA, LLP

(57) ABSTRACT

An information processing system includes a storage device configured to store therein information of a trained model, and a processor. The processor performs a detection process based on the information of the trained model, and outputs position information detected in the detection process, the detection process being a process that detects the position information about an object from a detection image. The trained model is trained based on training data in which an object in a training image is added with multiple annotations, and is trained to output position information about the object in the training image based on an overlapping relationship of the multiple annotations.

11 Claims, 17 Drawing Sheets

(51) Int. Cl.
    *G06T 5/00*     (2006.01)
    *G06T 7/00*     (2017.01)
    *A61B 1/00*     (2006.01)
    *G06F 18/214*   (2023.01)
    *G06V 10/774*   (2022.01)
    *G06V 10/80*    (2022.01)

(52) U.S. Cl.
    CPC ............... *G06N 3/08* (2013.01); *G06T 5/002* (2013.01); *G06T 7/0012* (2013.01); *G06V 10/774* (2022.01); *G06V 10/809* (2022.01); *G06T 2207/10068* (2013.01); *G06T 2207/20081* (2013.01); *G06T 2207/20084* (2013.01)

(58) Field of Classification Search
    CPC . G06T 7/0014; G06T 3/4046; G06T 2210/41; G06T 5/002; G06T 2207/10068; G16H 30/40; G06V 10/809; G06V 10/774; A61B 1/000096; G06F 18/214; G06N 3/08

See application file for complete search history.

(56) References Cited

U.S. PATENT DOCUMENTS

| | | | |
|---|---|---|---|
| 2014/0341449 A1* | 11/2014 | Tizhoosh | A61B 8/565 |
| | | | 382/128 |
| 2015/0131882 A1 | 5/2015 | Mohr et al. | |
| 2015/0238148 A1* | 8/2015 | Georgescu | G06F 18/28 |
| | | | 600/408 |
| 2018/0218495 A1* | 8/2018 | Ben-Ari | G06T 7/0014 |
| 2019/0250891 A1* | 8/2019 | Kumar | G06F 18/2411 |
| 2020/0226422 A1* | 7/2020 | Li | G06N 3/08 |
| 2021/0287395 A1* | 9/2021 | Ishikake | G06V 10/764 |
| 2021/0322121 A1* | 10/2021 | Venkataraman | A61B 34/25 |

FOREIGN PATENT DOCUMENTS

| | | |
|---|---|---|
| JP | 2015-93192 A | 5/2015 |
| JP | 2016-513328 A | 5/2016 |
| JP | 6182242 B1 | 8/2017 |

OTHER PUBLICATIONS

International Search Report dated Jun. 25, 2019, issued in counterpart International Application No. PCT/JP2019/013605, with English Translation. (4 pages).

* cited by examiner

FIG. 14
BEFORE ANNOTATION
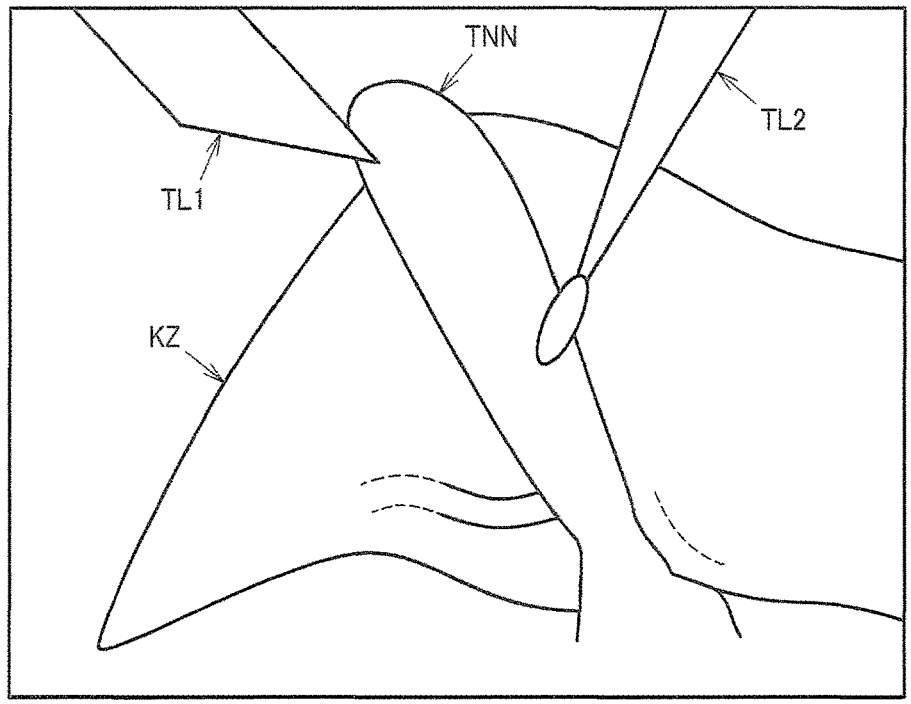
AFTER ANNOTATION
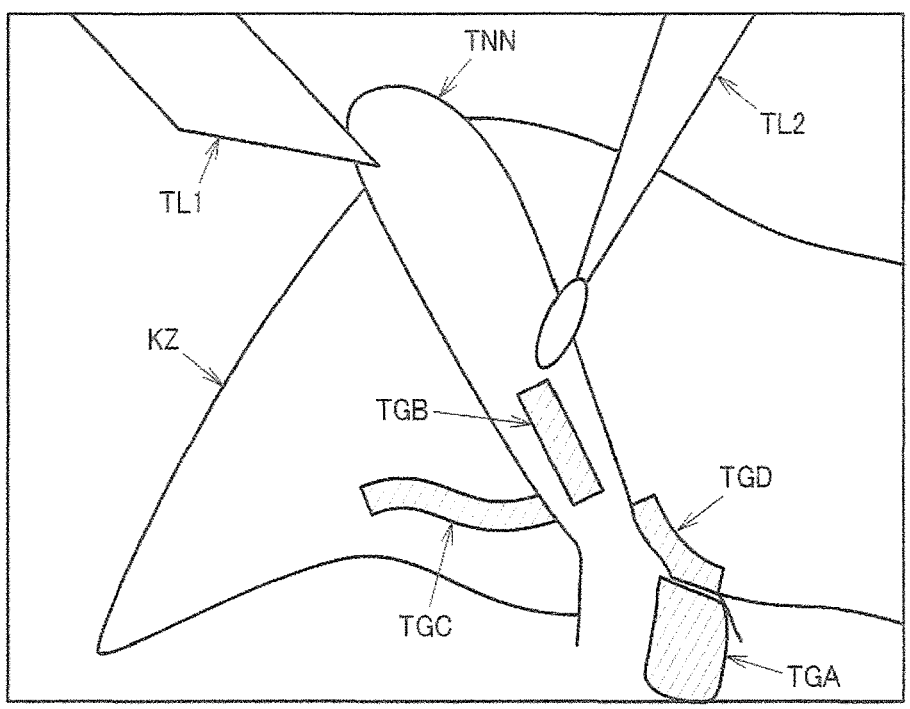

INFORMATION PROCESSING SYSTEM, ENDOSCOPE SYSTEM, INFORMATION STORAGE MEDIUM, AND INFORMATION PROCESSING METHOD

CROSS REFERENCE TO RELATED APPLICATION

This application is a continuation of International Patent Application No. PCT/JP2019/013605, having an international filing date of, Mar. 28, 2019, which designated the United States, the entirety of which is incorporated herein by reference.

BACKGROUND

A method of performing a process of detecting a recognition target from an image using machine learning has been known. For example, Japanese Patent No. 6182242 discloses a technology of selecting preferable training data from a training result. The technology of Japanese Patent No. 6182242 classifies training data into first and second labeling models, which are multiple different pieces of data, trains a training model on each of the first and second labeling models, and selects preferable training data from the training result.

SUMMARY

In accordance with one of some aspect, there is provided an information processing system comprising:
  a storage device configured to store therein information of a trained model; and
  a processor configured to perform a detection process based on the information of the trained model and output position information detected in the detection process, the detection process being a process that detects the position information about an object from a detection image,
  wherein the trained model is trained based on training data in which an object in a training image is added with multiple annotations, and is trained to output position information about the object in the training image based on an overlapping relationship of the multiple annotations.

In accordance with one of some aspect, there is provided an endoscope system comprising:
  a processor unit including the information processing system;
  an endoscopic scope connected to the processor unit, and configured to capture the detection image and transmit the detection image to the processor unit; and
  a display device connected to the processor unit, and configured to display the detection image on which display information indicating a position of the object is superimposed, based on the position information about the object detected from the detection image by the information processing system.

In accordance with one of some aspect, there is provided a non-transitory information storage medium configured to store therein a trained model,
  wherein the trained model causes a computer to perform a detection process of receiving an input of a detection image to a neural network and detecting an object, and to output position information detected by the detection process,
  wherein the neural network comprises:
    an input layer configured to take input data;
    an intermediate layer configured to perform arithmetic processing on the data input through the input layer; and
    an output layer configured to output data based on a result of the arithmetic processing output from the intermediate layer, and
  wherein the trained model is trained based on training data in which an object in a training image is added with multiple annotations, and is trained to output position information about the object in the training image based on an overlapping relationship of the multiple annotations.

In accordance with one of some aspect, there is provided an information processing method of performing a detection process based on a trained model,
  wherein the trained model is trained based on training data in which an object in a training image is added with multiple annotations, and is trained to output position information about the object in the training image based on an overlapping relationship of the multiple annotations, and
  wherein the information processing method comprises:
    performing the detection process of detecting position information about an object from a detection image; and
    outputting the position information detected by the detection process.

BRIEF DESCRIPTION OF THE DRAWINGS

FIG. 14 illustrates an example of annotation.

DESCRIPTION OF EXEMPLARY EMBODIMENTS

Figure 1:
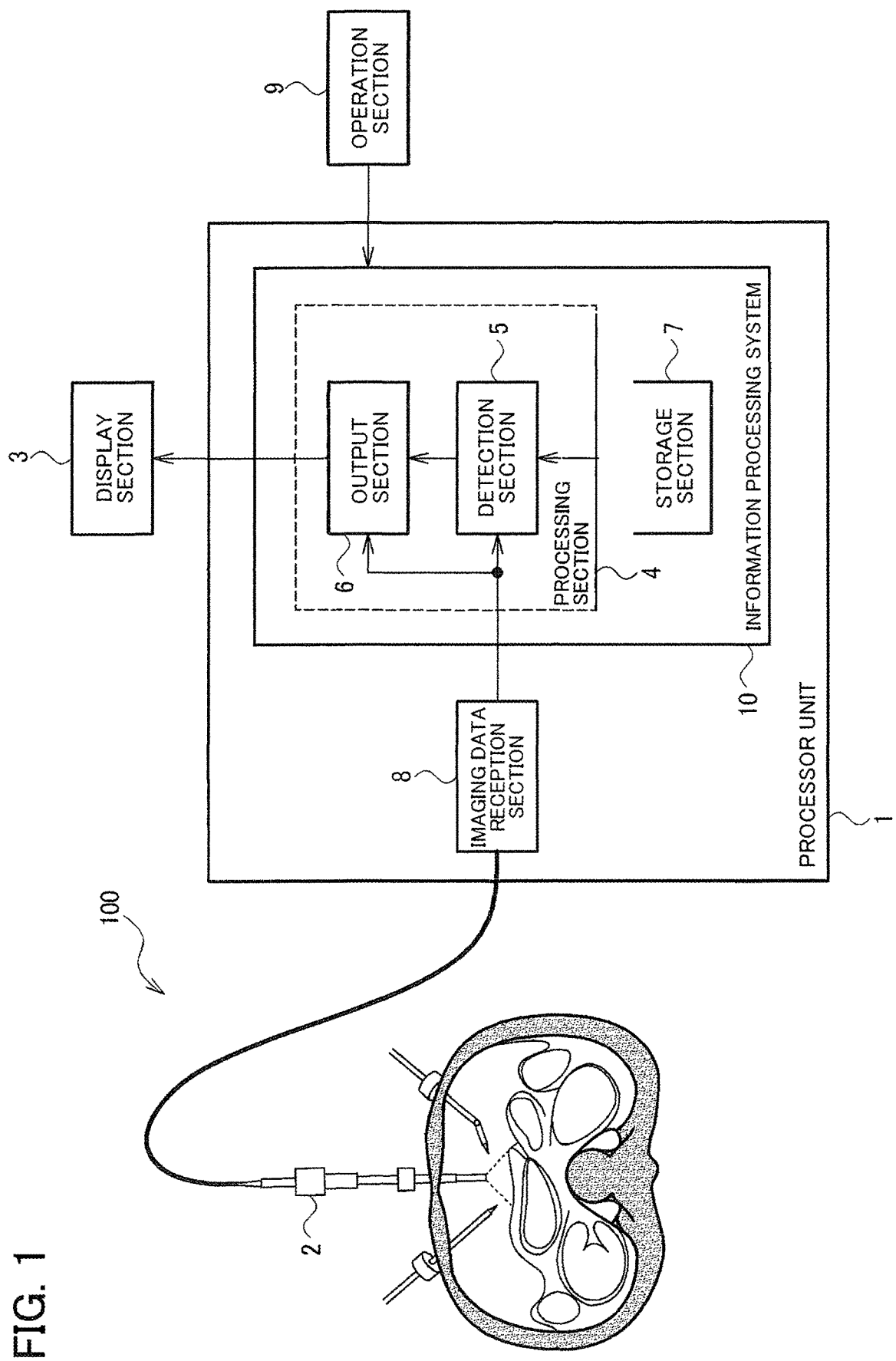
FIG. 1 illustrates a configuration example of an information processing system and an endoscope system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Information Processing System and Endoscope System

FIG. 1 illustrates a configuration example of an information processing system 10, and an endoscope system 100 including the information processing system 10, in accordance with the present embodiments. The endoscope system 100 includes a processor unit 1, an endoscopic scope 2, and a display section 3. The endoscope system 100 may further include an operation section 9.

An imaging device is arranged at a distal end of the endoscopic scope 2, and the distal end is inserted into an abdominal cavity. The imaging device captures an image of the inside of the abdominal cavity, and the captured image is transmitted from the endoscopic scope 2 to the processor unit 1.

The processor unit 1 is a device that performs various processes in the endoscope system 100. For example, the processor unit 1 performs control of the endoscope system 100, image processing, and the like. The processor unit 1 includes an imaging data reception section 8 that receives imaging data from the endoscopic scope 2, and the information processing system 10 that detects an object from the imaging data by a trained model.

The imaging data reception section 8 is, for example, a connector to which a cable of the endoscopic scope 2 is connected, an interface circuit that receives imaging data, or the like.

The information processing system 10 includes a storage section 7 that stores therein a trained model, and a processing section 4 that detects the object from an image based on the trained model stored in the storage section 7. The image used for detecting the object is hereinafter referred to as a detection image. In the configuration example of FIG. 1, the imaging data output from the imaging data reception section 8 to the processing section 4 corresponds to the detection image.

The storage section 7 is, for example, a storage device such as a semiconductor memory, a hard disk drive or an optical disk drive. The trained model is preliminarily stored in the storage section 7. Alternatively, the trained model may be input to the information processing system 10 from an external device such as a server via a network, to be stored in the storage section 7.

The processing section 4 includes a detection section 5 and an output section 6. The detection section 5 detects the object from the image by making an inference by the trained model. The output section 6 superimposes display information on the image based on a result of the detection, and causes the display section 3 to display the image. The display information is information indicating a position of the object. Various kinds of hardware can be assumed as hardware to make an inference by the trained model. For example, the detection section 5 is a general-purpose processor such as a central processing unit (CPU). In this case, the trained model stored in the storage section 7 is composed of a program describing an inference algorithm and a parameter to be used for the inference algorithm. Alternatively, the detection section 5 may be a dedicated processor that implements the inference algorithm as hardware. The dedicated processor is, for example, an application-specific integrated circuit (ASIC), a field-programmable gate array (FPGA), or the like. In this case, the trained model stored in the storage section 7 is composed of a parameter to be used for the inference algorithm. A neural network may be applied to the inference algorithm. In this case, the parameter is a weight coefficient assigned between connected nodes in the neural network.

The display section 3 is a monitor to display the image output from the output section 6, and is, for example, a display device such as a liquid crystal display, an organic electroluminescence (EL) display, or the like.

The operation section 9 is a device for an operator to operate the endoscope system 100. The operation section 9 is, for example, a button, a dial, a foot switch, a touch panel, or the like.

While the information processing system 10 is included in the processor unit 1, part or all of the information processing system 10 may be arranged outside the processor unit 1. For example, the storage section 7 and the detection section 5 may be implemented by an external processing device such as a personal computer (PC) or a server. Alternatively, the storage section 7 and the detection section 5 may be implemented by a cloud system in which parallel processing is performed by multiple PCs, multiple servers, or the like connected via a network. The imaging data reception section 8 transmits imaging data to the external processing device or the cloud system via the network or the like. The external processing device or the cloud system transmits information indicating the detected object to the output section 6 via the network or the like. The output section 6 superimposes the received information on the image, and causes the display section 3 to display the image.

A captured image of a general object shows a clear boundary of the object. In implementing position detection of such an object by machine learning, the machine learning is performed by, for example, creating data in which the inside of the boundary is filled in and using the data and the image as training data. The boundary is clear enough for any person to identify a single boundary without ambiguity. Also in a case of detecting the object by the trained model, the boundary of the detection target object is clear enough to dispense with the need for ambiguous detection of the boundary.

In contrast, an image of the inside of the body captured by an endoscope includes an object having an ambiguous boundary. For example, this occurs when the object is present within the angle of view but is hidden by other tissues or organs, when the object is visible in the image but has an unclear boundary, or in other like cases. In implementing position detection of such an object by machine learning, the boundary may be determined differently if various operators are involved in creation of training data. Furthermore, in detecting the object by the trained model, it is preferable that the boundary of the detection target object be detectable while permitting ambiguity. Note that an operator who creates the training data is, for example, a doctor or the like who performs diagnosis or treatment using the endoscope system 100.

For an object having an ambiguous boundary in a medical image, a description will be given below of methods of the present embodiments capable of detecting a position of such an object in consideration of ambiguity of a boundary by giving multiple annotations to the object.

2. First Embodiment

Figure 2:
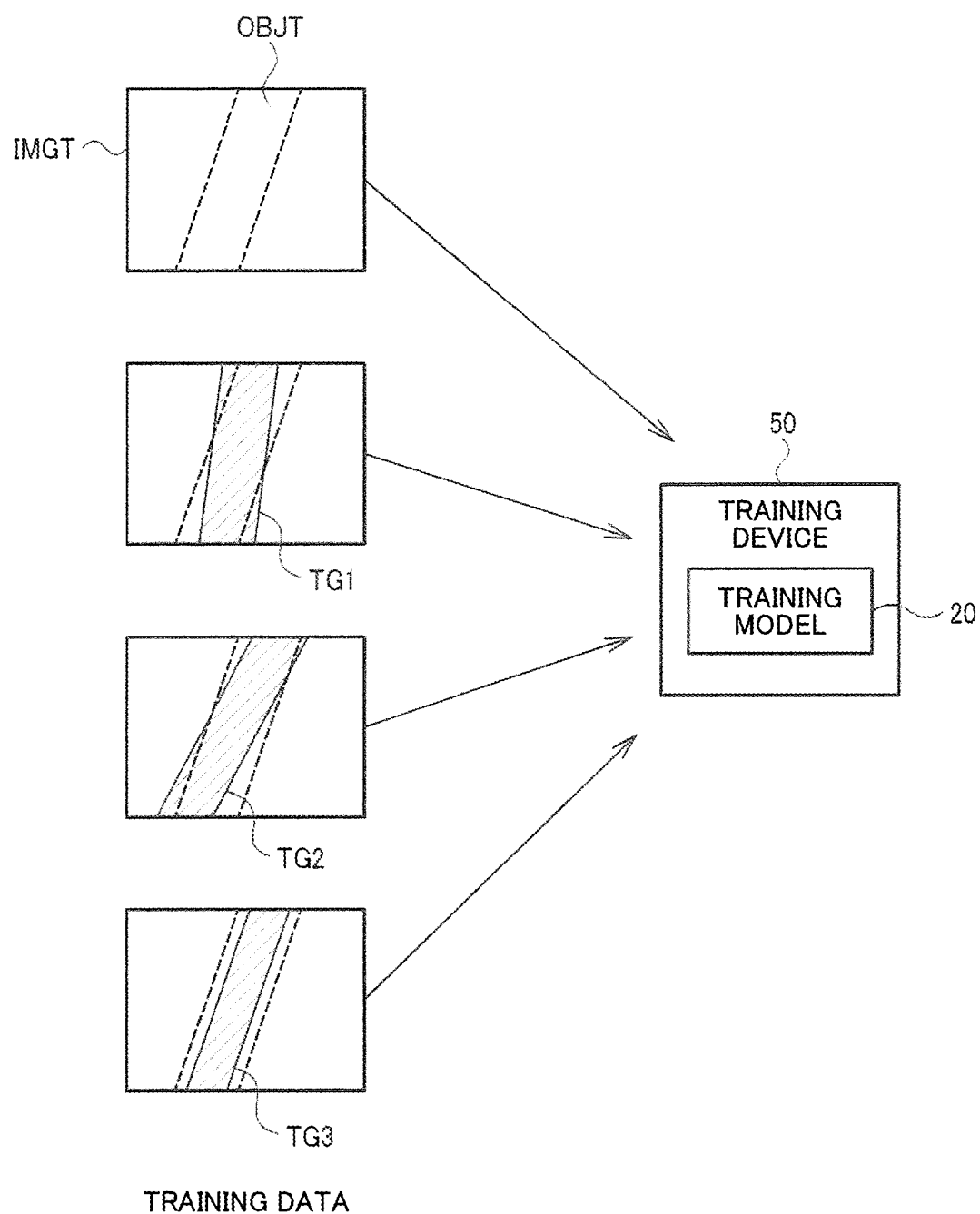
FIG. 2 illustrates a training process in accordance with a first embodiment.

FIG. 2 illustrates a training process in accordance with a first embodiment. An image to be used for the training process is hereinafter referred to as a training image. The training image is, for example, a frame image of a video captured by an endoscope system.

A training image IMGT includes, within its angle of view, an object OBJT having an ambiguous boundary. In FIG. 2, the ambiguous boundary is indicated by a dotted line. Note that in a case where the object OBJT is covered with other tissues or organs, the object OBJT itself cannot be visually recognized in the training image IMGT, but the object in this case also falls within the object OBJT having the ambiguous boundary.

The training data includes the training image IMGT and multiple annotations TG1 to TG3. The annotations TG1 to TG3 are added to the identical object OBJT in the identical training image IMGT. Note that the identical object in the identical image only needs to be added with first to n-th annotations, where n is an integer of two or greater. In the following description, assume that n is three.

The annotations TG1 to TG3 are added by respective different operators. The ambiguous boundary of the object causes the operators to determine the boundary variously, so that the positions and shapes of the annotations TG1 to TG3 are different from one another. As described later with reference to FIGS. 14 and 15, the annotations TG1 to TG3 are map data in which a flag is set to each pixel. The flag is set to each pixel in a region determined to be the object OBJT by an operator. This map data is hereinafter also referred to as flag data.

A training device 50 performs the training process on a training model 20 using training data. That is, the training device 50 inputs the training image IMGT to the training model 20, compares position information about the object OBJT detected by the training model 20 with the annotation TG1, and gives feedback based on an error thereof to the training model 20. The training device 50 sequentially performs this procedure also with respect to the annotations TG2 and TG3.

Note that a training method is not limited to the above-described method. For example, the training device 50 may combine the annotations TG1 to TG3 to generate a combined annotation, and perform the training process of the training model 20 based on the combined annotation and the training image IMGT. For example, the training device 50 may perform addition-averaging on pieces of map data of the annotations TG1 to TG3 to generate the combined annotation. For example, assume that a flag "1" is set to each pixel of the annotations TG1 to TG3. For example, with respect to a pixel to which all of the annotations TG1 to TG3 set the flag, the average flag value is one. With respect to a pixel to which only one of the annotations TG1 to TG3 sets the flag, the average flag value is one-third. Map data in which such an average value is set to each pixel is the combined annotation.

Performing the training illustrated in FIG. 2 trains the training model 20 to output the position information about the object OBJT in the training image IMGT based on an overlapping relationship of the multiple annotations TG1 to TG3. Specifically, the position information about the object OBJT is information indicating a probability of the position of the object OBJT in a continuous or stepwise manner. The training model 20 after the training outputs position information with a higher probability of the position in a region where the annotations TG1 to TG3 overlap, and with a lower probability of the position in a region where the annotations TG1 to TG3 do not overlap. The training model 20 after the training is hereinafter referred to as a trained model.

Figure 3:
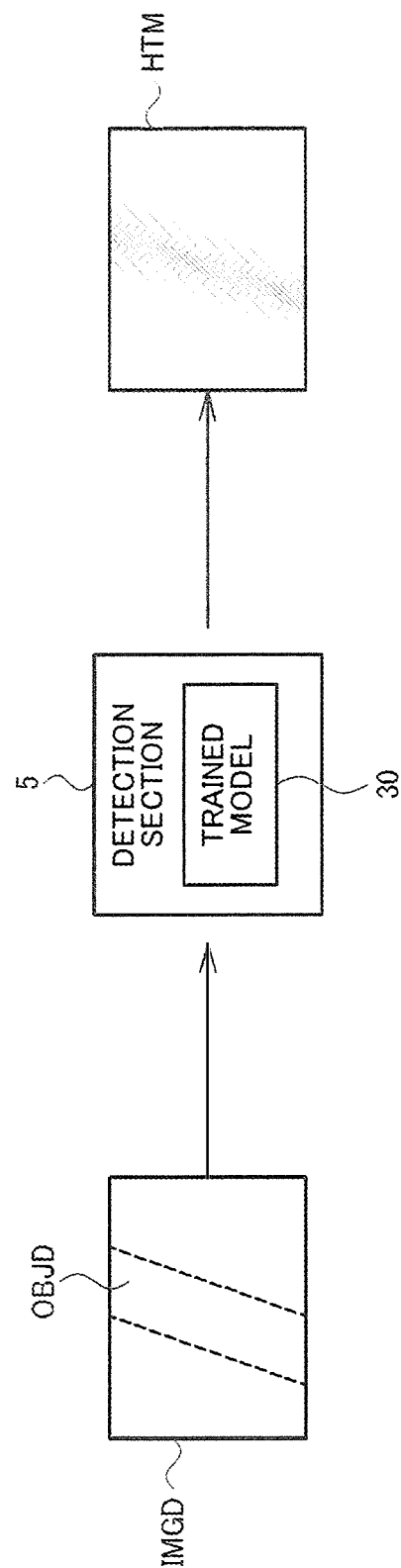
FIG. 3 illustrates a detection process in accordance with the first embodiment.

FIG. 3 illustrates a detection process in accordance with the first embodiment. A detection image IMGD is, for example, a frame image of a movie captured by the endoscope system 100.

The detection image IMGD includes, within its angle of view, an object OBJD having an ambiguous boundary. In FIG. 3, the ambiguous boundary is indicated by a dotted line. Note that in a case where the object OBJD is covered with other tissues or organs, the object OBJD itself cannot be visually recognized in the detection image IMGD, but the object in this case also falls within the object OBJD having the ambiguous boundary. FIG. 3 illustrates a case where the position and shape of the object OBJD is the same as the position and shape of the object OBJT in the training image IMGT. Usually, however, the detection image IMGD is different from the training image IMGT, and the position and shape of the object OBJD is different from the position and shape of the object OBJT.

The detection section 5 detects position information about the object OBJD from the detection image IMGD. That is, the detection section 5 inputs the detection image IMGD to a trained model 30, and outputs position information HTM about the object OBJD detected by the trained model 30. The position information HTM is information indicating a probability of the position of the object OBJD in a continuous or stepwise manner. Specifically, the position information HTM is map data in which a value indicating the probability of the position is allocated to each pixel. In FIG. 3, the probability of the position of the position information HTM is represented by hatching. The higher density of hatch lines indicates the higher probability of the position. FIG. 3 illustrates the position information with three steps of probability. Actually, however, the number of steps of probability is not limited to three, or instead, the probability may be a continuous value.

Figure 4:
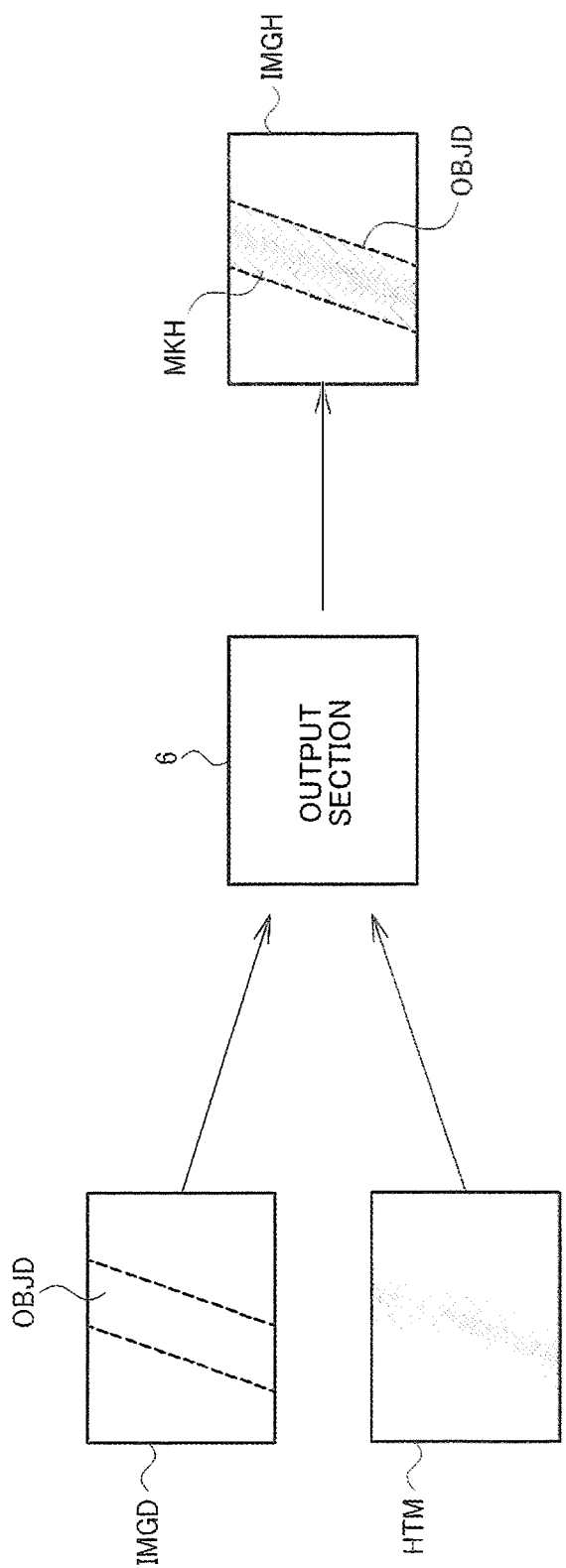
FIG. 4 illustrates a display process in accordance with the first embodiment.

FIG. 4 illustrates a display process in accordance with the first embodiment.

The output section 6 generates a display image IMGH based on the detection image IMGD and the position information HTM, and outputs the display image IMGH to the display section 3. Specifically, the output section 6 generates display information MKH based on the position information HTM, and generates the display image IMGH by superimposing the display information MKH on the detection image IMGD. The display information MKH is information indicating a probability of the position of the object OBJD in a continuous or stepwise manner. For example, the display information MKH is heat map that visualizes a value of the probability by color variation. Alternatively, the display information MKH may be monochrome information whose transmittance varies in accordance with the value of the probability.

In the present embodiment, the trained model 30 is generated through training of the training model 20 based on the training data in which the multiple annotations TG1 to TG3 are added to the object OBJT in the training image IMGT. As a result, the trained model 30 can output the position information about the object OBJT based on the overlapping relationship of the multiple annotations TG1 to TG3. The resulting training data can contain individual annotations added to the identical object individually by the multiple operators. In addition, through the training based on the overlapping relationship of the multiple annotations TG1 to TG3, the present embodiment can perform training in consideration of ambiguity of the boundary of the object OBJT.

Further in accordance with the present embodiment, using the trained model 30 that has been trained based on the overlapping relationship of the multiple annotations TG1 to TG3 enables detection of the position information HTM that indicates the probability of the position of the object OBJD in the detection image IMGD in a continuous or stepwise manner. Based on the position information HTM, the output section 6 can cause the display section 3 to display the display information MKH that indicates the probability of the position of the object OBJD in the detection image IMGD in a continuous or stepwise manner. In this manner, the present embodiment can display the position information in consideration of ambiguity of the boundary of the object OBJD.

3. Second Embodiment

A second embodiment is similar to the first embodiment in detection of the position information in consideration of ambiguity of the boundary, but the processing in consideration of ambiguity of the boundary is performed on the output side.

Figure 5:
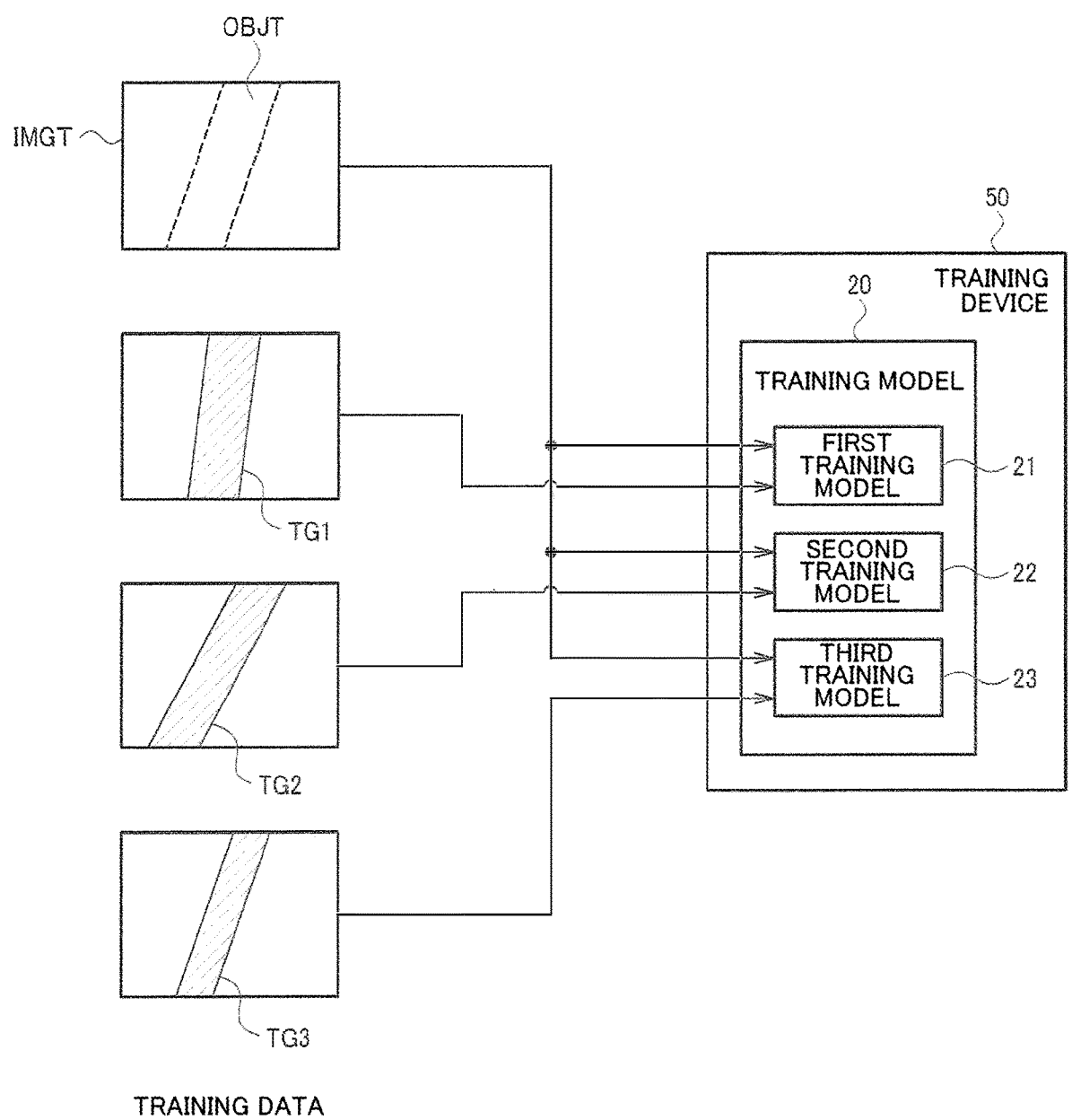
FIG. 5 illustrates a training process in accordance with a second embodiment.

FIG. 5 illustrates a training process in accordance with the second embodiment. The training data includes the training image IMGT and the multiple annotations TG1 to TG3 similarly to the first embodiment.

The training model 20 includes a first training model 21, a second training model 22, and a third training model 23. The training models 21 to 23 use, for example, an identical inference algorithm, but are not so limited. The training device 50 performs the training process of the training models 21 to 23 using training data. That is, the training device 50 inputs the training image IMGT to the training model 21, compares first position information about the object OBJT detected by the training model 21 with the annotation TG1, and gives feedback based on an error thereof to the training model 21. Similarly, the training device 50 inputs the training image IMGT to the training models 22, 23, respectively, compares second and third position information about the object OBJT detected by the training models 22, 23 with the annotations TG2, TG3, and gives feedback based on errors thereof to the training models 22, 23.

By the training described above, the training model 21 is trained to output the first position information similar to the annotation TG1. That is, the training model 21 is trained to output flag data similar to the flag data of the annotation TG1, as the first position information. Similarly, the training models 22, 23 are respectively trained to output flag data similar to the flag data of the annotations TG2, TG3, as the second and third position information.

Since the position information output by each of the training models 21 to 23 is flag data, each piece of the position information provides a clear boundary. In contrast, for the training model 20 as a whole, the three pieces of flag data corresponding to the respective annotations TG1 to TG3 provide position information in consideration of ambiguity of the boundary of the object OBJT.

Figure 6:
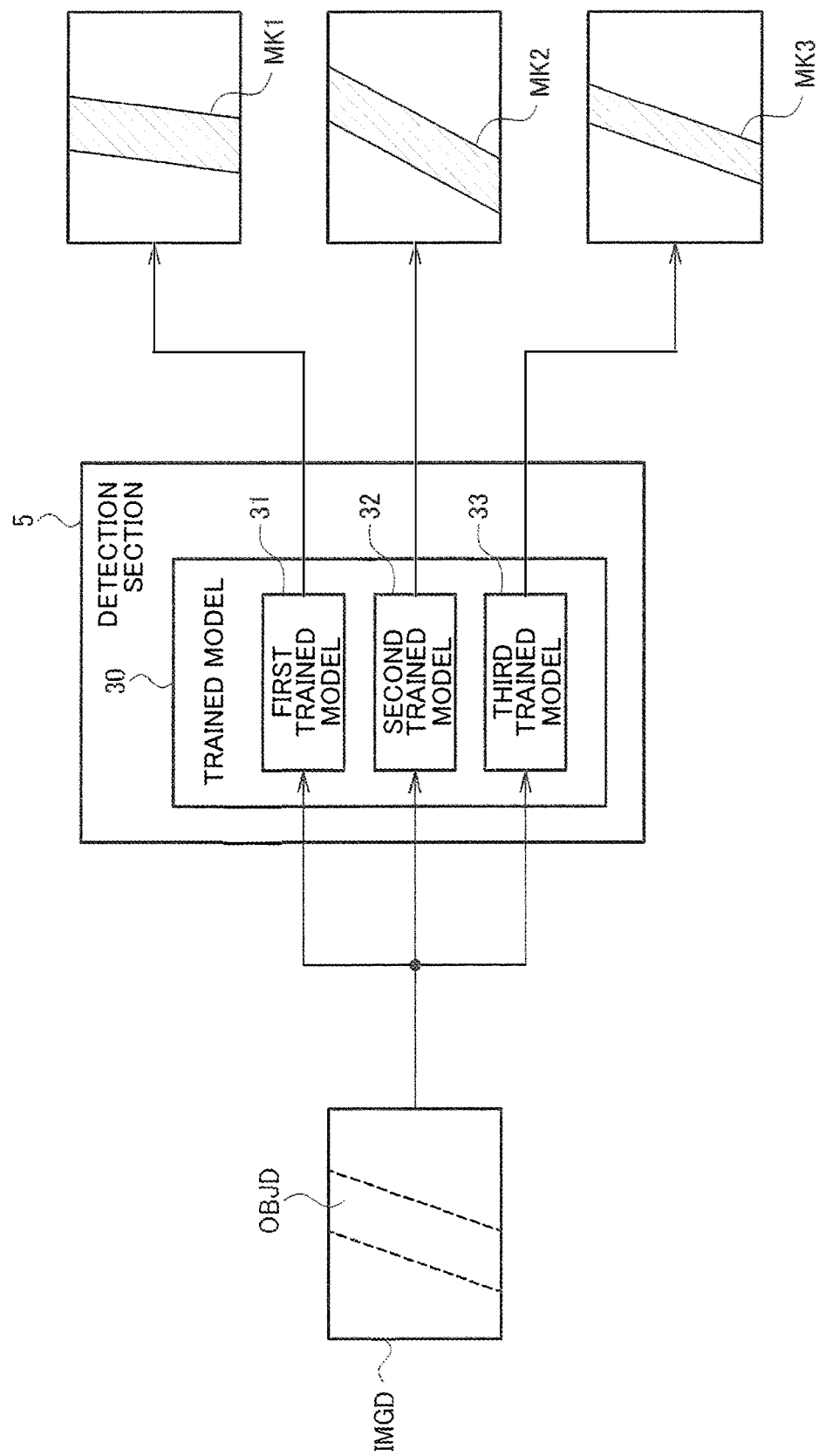
FIG. 6 illustrates a detection process in accordance with the second embodiment.

FIG. 6 illustrates a detection process in accordance with the second embodiment. The trained model 30 includes first to third trained models 31 to 33. The trained models 31 to 33 correspond to the training models 21 to 23 after the training, respectively.

The detection section 5 detects first to third position information MK1 to MK3 about the object OBJD from the detection image IMGD. That is, the detection section 5 inputs the detection image IMGD to the trained model 31, and outputs the position information MK1 detected by the trained model 31. Similarly, the detection section 5 inputs the detection image IMGD to the trained models 32, 33, respectively, and outputs the position information MK2, MK3 detected by the trained models 32, 33. The position information MK1 to MK3 is map data in which a flag is set to each pixel, and thus is flag data.

Figure 7:
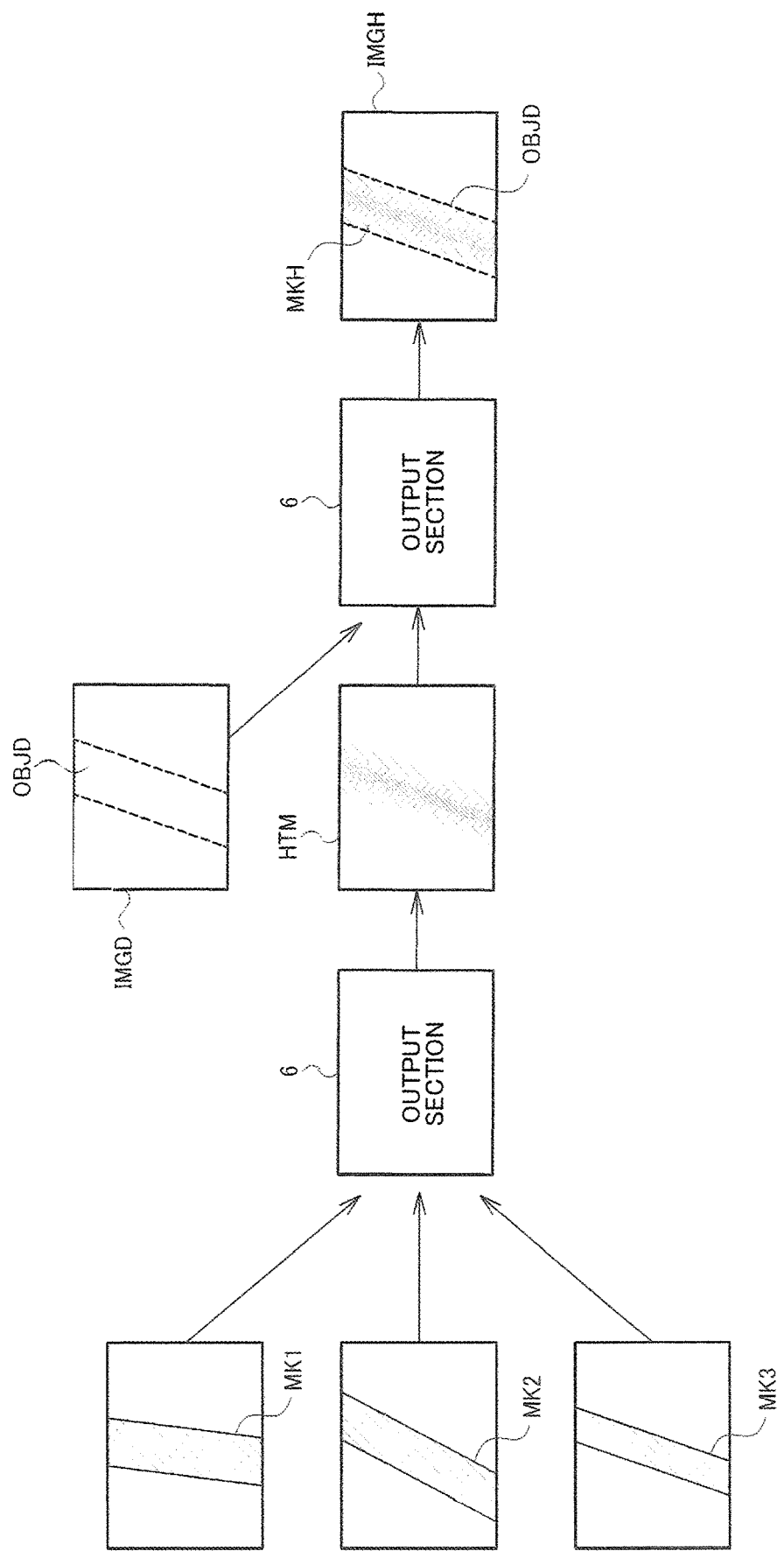
FIG. 7 illustrates a display process in accordance with the second embodiment.

FIG. 7 illustrates a display process in accordance with the second embodiment.

The output section 6 outputs the position information HTM about the object OBJD based on the position information MK1 to MK3. The position information HTM is information indicating the probability of the position of the object OBJD in a continuous or stepwise manner. That is, as the position information HTM, the output section 6 generates map data in which a value indicating the probability of the position is allocated to each pixel. For example, the output section 6 performs addition-averaging on the position information MK1 to MK3 to generate the map data.

The output section 6 generates the display image IMGH based on the detection image IMGD and the position information HTM, and outputs the display image IMGH to the display section 3. The display image IMGH is generated just as in the first embodiment.

In accordance with the present embodiment, since the position information MK1 to MK3 respectively detected by the trained models 31 to 33 is flag data, each piece of the position information provides a clear boundary. In contrast, the position information HTM obtained by combining the position information MK1 to MK3 by the output section 6 indicates the probability of the position in a continuous or stepwise manner. Using this position information HTM, the present embodiment can display the position information in consideration of ambiguity of the boundary of the object OBJD.

4. Third Embodiment

A third embodiment assigns weights to the annotations TG1 to TG3, and performs training using the weighted annotations TG1 to TG3.

Figure 8:
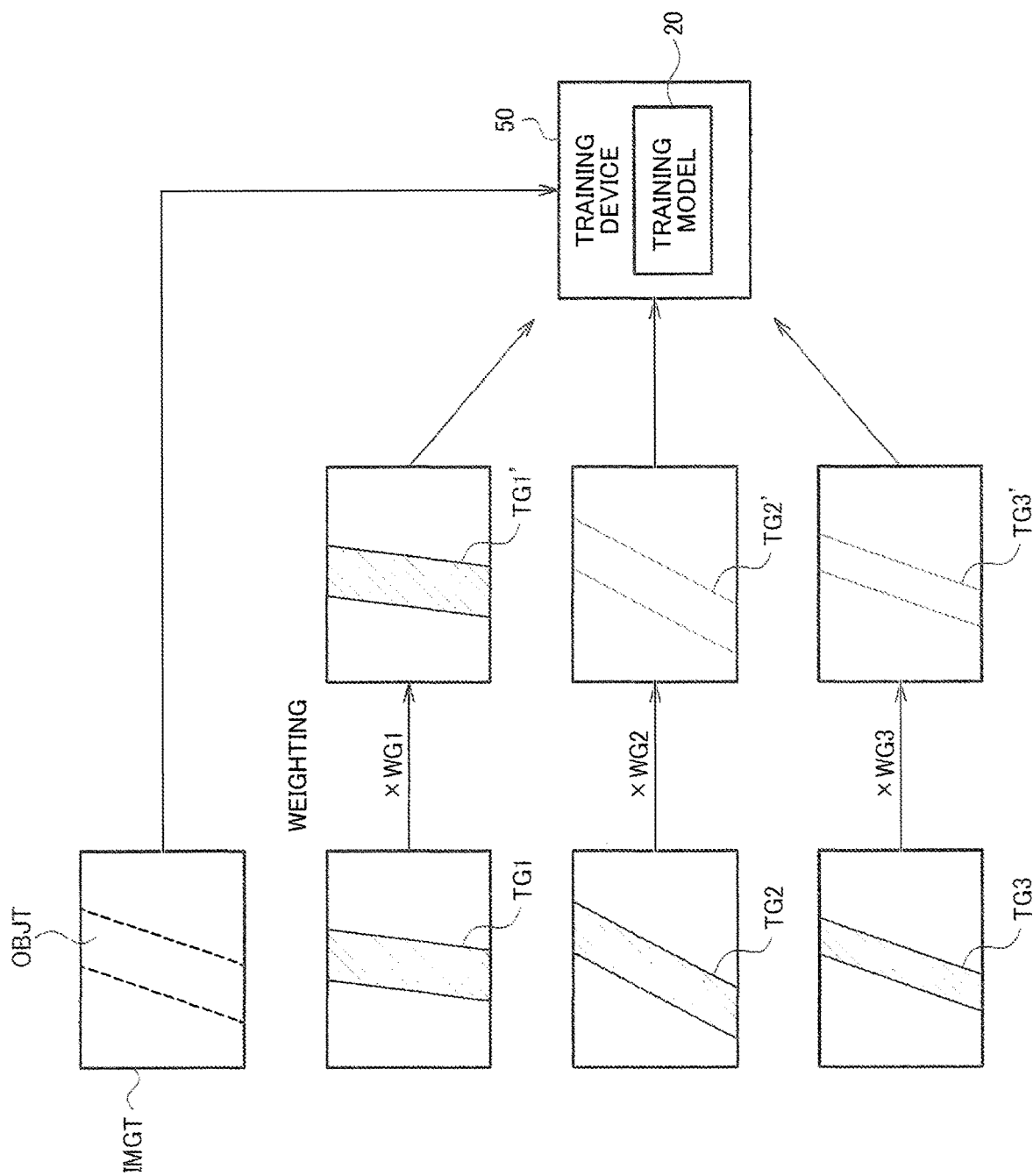
FIG. 8 illustrates a training process in accordance with a third embodiment.

FIG. 8 illustrates a training process in accordance with the third embodiment. The training data includes the training image IMGT and the multiple annotations TG1 to TG3 similarly to the first embodiment.

The training device 50 assigns weights to the annotations TG1 to TG3 to generate annotations TG1' to TG3'. Among the annotations TG1 to TG3, the training device 50 assigns a higher weight to an annotation of highest importance. For example, when the annotations TG1 to TG3 have been created by three operators, an annotation created by the most proficient operator is weighted more highly. While various weighting processes can be specifically assumed, the following first and second examples can be given as examples.

In the first example, the training device 50 multiplies respective pieces of flag data of the annotations TG1 to TG3 by weight coefficients WG1 to WG3, respectively, to generate the annotations TG1' to TG3'. For example, to a pixel flagged as "1" in TG1, a value "WG1" is allocated in TG1'. For example, in a case where emphasis is placed on the annotation TG1, WG1 is set greater than WG2 and WG3 (WG1>WG2, and WG1>WG3).

In the second example, the training device 50 generates the annotations TG1' to TG3' by processing the respective positions and shapes of the annotations TG1 to TG3 to approximate to the position and shape of the most important annotation. For example, in a case where emphasis is placed on the annotation TG1, the training device 50 approximates the positions and shapes of the annotations TG2, TG3 to the position and shape of the annotation TG1. For example, the training device 50 multiplies the respective pieces of flag data of the annotations TG2, TG3 by the piece of flag data of the annotation TG1 as a weight coefficient, and thereby generates the annotations TG2', TG3'. This process keeps only portions of the annotations TG2 and TG3 that overlap with the annotation TG1 as the annotations TG2' and TG3'. The annotation TG1' is identical to the annotation TG1.

The training device 50 performs a training process using the annotations TG1' to TG3' similarly to the training process in the first embodiment described with reference to FIG. 2.

In addition, the detection section 5 detects the position information HTM about the object OBJD from the detection image IMGD similarly to the detection process in the first embodiment described with reference to FIG. 3. Furthermore, the output section 6 generates the display image IMGH based on the position information HTM about the object OBJD and the detection image IMGD similarly to the display process in the first embodiment described with reference to FIG. 4.

The training performed in the present embodiment is based on the training data in which the overlapping relationship among the multiple annotations TG1 to TG3 is weighted. This training can thus place emphasis on, for example, an annotation created by a proficient operator. The present embodiment uses the trained model 30 created by this training to detect the position information about the object OBJD from the detection image IMGD, and can thereby provide a detection result that reflects knowledge of the proficient operator more significantly.

Note that "the overlapping relationship is weighted" means that the multiple annotations are weighted by importance of their mutual overlapping relationship. In the first example described above, the annotation TG1 is weighted most highly, and hence portions of the annotations TG2 and TG3 that do not overlap with the annotation TG1 are less influential on the training. In the second example described above, the annotations TG2 and TG3 are processed to keep only the portions overlapping with the annotation TG1. That is, the portions that overlap with the annotation TG1 are treated as more important portions in the annotations TG2 and TG3.

5. Fourth Embodiment

A fourth embodiment assigns weights similarly to the third embodiment, but weights are assigned to multiple pieces of position information detected by the trained model 30.

Figure 9:
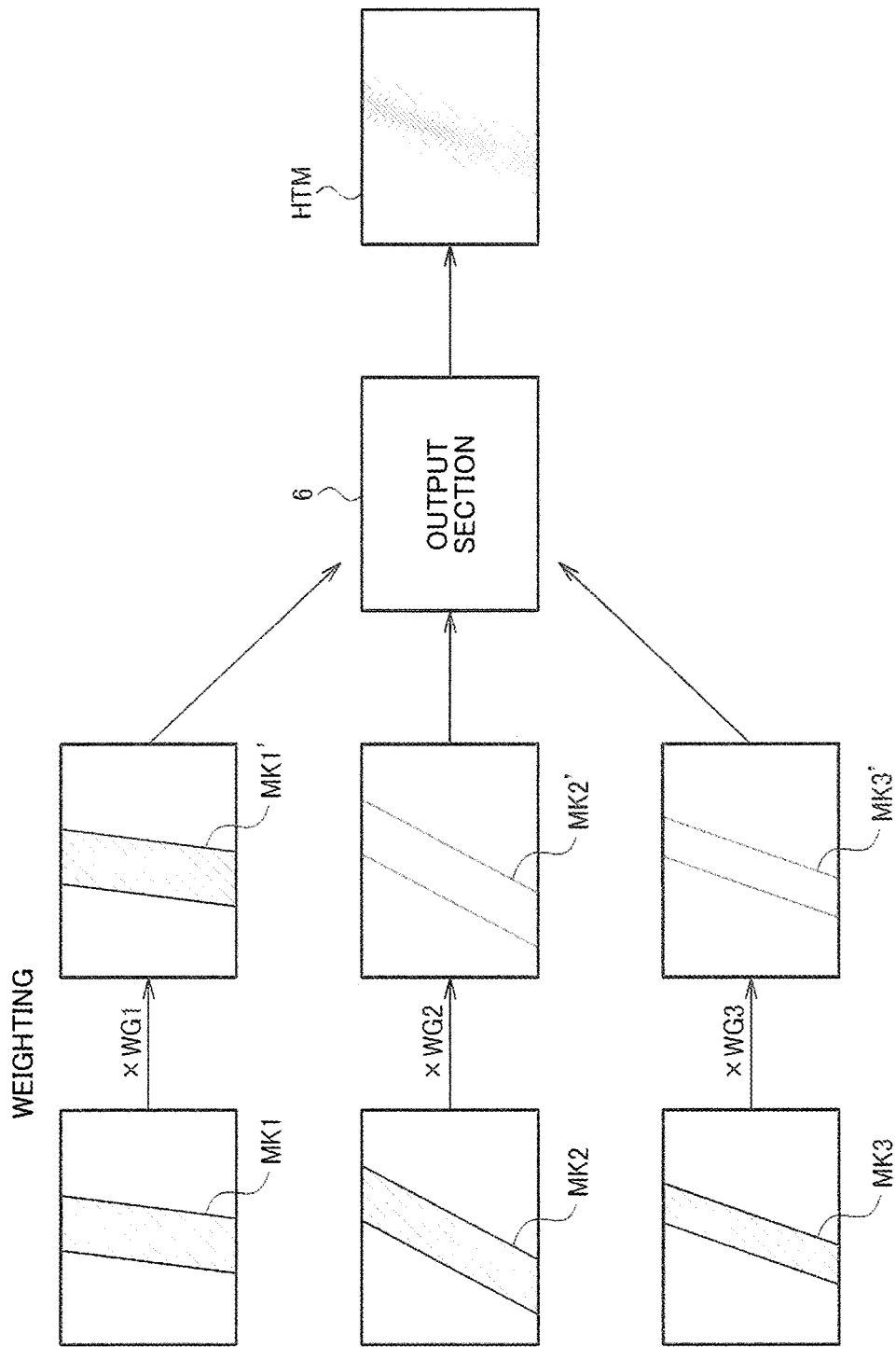
FIG. 9 illustrates a detection process and a display process in accordance with a fourth embodiment.

FIG. 9 illustrates a detection process and a display process in accordance with the fourth embodiment. Similarly to the second embodiment, the trained model 30 includes the first trained model 31, the second trained model 32, and the third trained model 33. That is, the detection section 5 inputs the detection image IMGD to the trained models 31 to 33, and outputs the position information MK1 to MK 3 detected by the trained models 31 to 33, respectively.

The output section 6 assigns weights to the position information MK1 to MK3 to generate position information MK1' to MK3', respectively. The output section 6 assigns weights to the position information MK1 to MK3 similarly to the application of weights to the annotations TG1 to TG3 in the third embodiment. That is, the output section 6 assigns a higher weight to a piece of position information corresponding to an annotation that is desirable to be considered important. The output section 6 generates the position information HTM from the weighted position information MK1' to MK3'. For example, the output section 6 performs addition-averaging on the weighted position information MK1' to MK3' to generate map data. The output section 6 generates the display image IMGH based on the position information HTM about the object OBJD and the detection image IMGD similarly to the display process in the first embodiment described with reference to FIG. 4.

The present embodiment assigns weights to the position information MK1 to MK3 detected by the trained models 31 to 33, respectively, to generate the position information HTM. The present embodiment can thus generate the position information HTM with emphasis on, for example, an annotation created by a proficient operator, and can thereby provide a detection result that reflects knowledge of the proficient operator more significantly.

6. Fifth Embodiment

A fifth embodiment performs a blurring process based on an overlapping relationship of the annotations TG1 to TG3, and performs training using the annotations after the blurring process.

Figure 10:
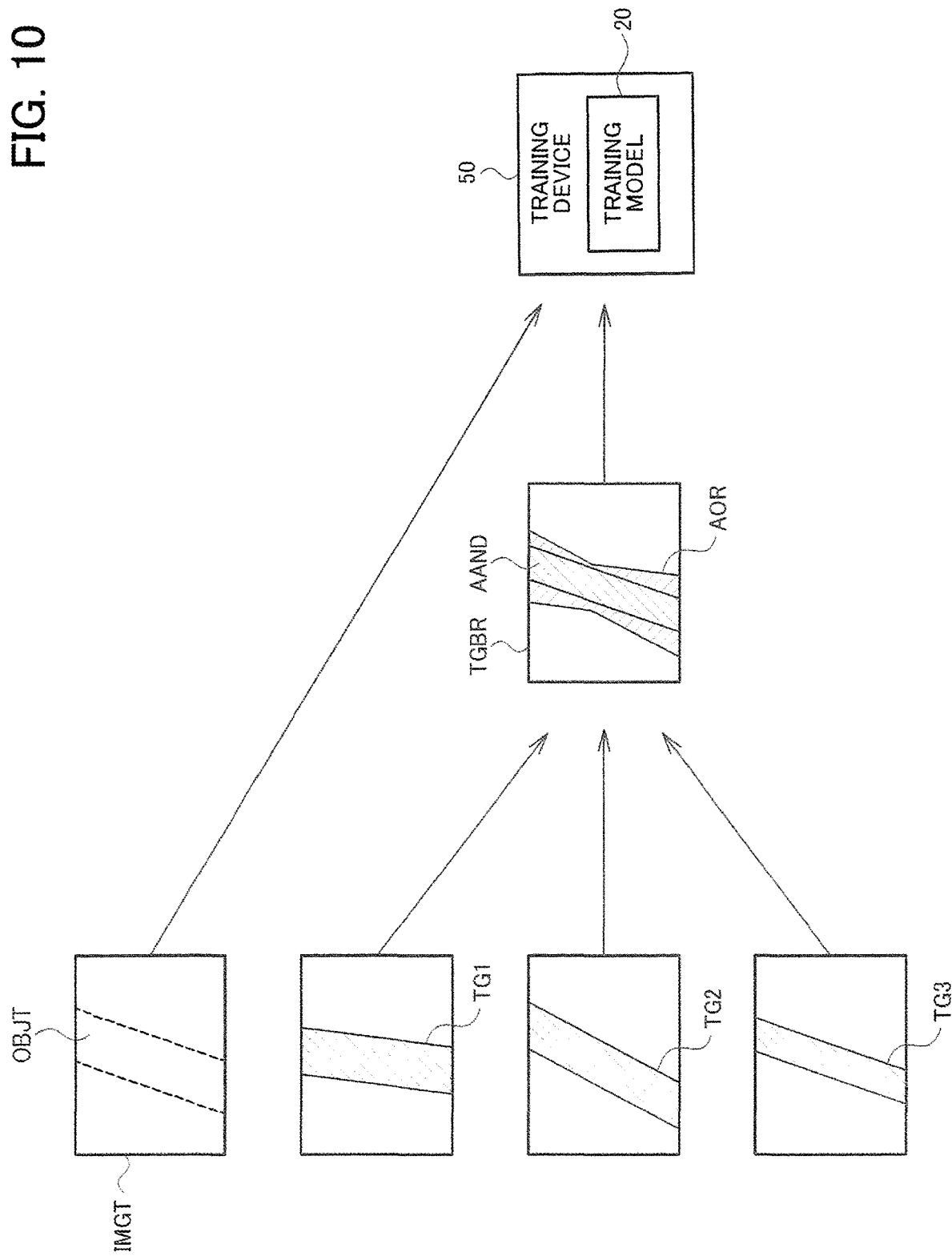
FIG. 10 illustrates a training process in accordance with a fifth embodiment.

FIG. 10 illustrates a training process in accordance with the fifth embodiment. The training device 50 performs the blurring process on the annotations TG1 to TG3 to generate an annotation TGBR. The training device 50 performs the training process on the training model 20 using the annotation TGBR after the blurring process and the training image IMGT. While the blurring process may be performed in various manners, one example is described below.

The training device 50 obtains a logical AND and a logical OR of the annotations TG1 to TG3. The training device 50 executes logical AND and logical OR operations with respect to each pixel in flag data, and outputs respective results of the logical AND and logical OR operations as flag data. A region corresponding to the logical AND of the annotations TG1 to TG3 is defined as a region AAND, and a region corresponding to the logical OR of the annotations TG1 to TG3 is defined as a region AOR. The training device 50 allocates a value of "1" to each pixel belonging to the region AAND, and performs the blurring process on the region AOR. The blurring process adds gradations to the region AOR. That is, in the region AOR, the training device 50 allocates a smaller value to a pixel farther from the region AAND.

Note that the blurring process is not limited to the one described above. For example, the training device 50 may perform the blurring process on each of the annotations TG1 to TG3 to generate annotations TG1" to TG3", and may perform the training process on the training model 20 using the annotations TG1" to TG3". For example, the training device 50 may perform the blurring process on the region AOR in each of the annotations TG1 to TG3 to generate the annotations TG1" to TG3". Alternatively, the training device 50 may perform a blurring process to blur the boundary in each of the annotations TG1 to TG3 to generate the annotations TG1" to TG3".

The blurring process on the region AOR or the blurring process on the boundary is implemented by, for example, a low-pass filter process. For example, the low-pass filter process can be performed on a specific region by using a mask designating a region where the blurring process is desired.

The detection process and the display process are similar to those in the first embodiment. That is, the detection section 5 detects the position information HTM about the object OBJD from the detection image IMGD similarly to the detection process in the first embodiment described with reference to the FIG. 3. Furthermore, the output section 6 generates the display image IMGH based on the position information HTM about the object OBJD and the detection image IMGD similarly to the display process in the first embodiment described with reference to FIG. 4.

The present embodiment trains the training model 20 based on the training data in which the blurring process is performed on a region where the multiple annotations TG1 to TG3 do not overlap, and thereby generates the trained model 30. The present embodiment uses the trained model 30 created by this training to detect the position information about the object OBJD from the detection image IMGD, and can thereby display the position information in consideration of ambiguity of the boundary of the object OBJD. Note that the "region where the multiple annotations TG1 to TG3 do not overlap" means a region where at least one of the annotations TG1 to TG3 does not overlap with the rest, and corresponds to a region excluding the region AAND from the region AOR.

7. Sixth Embodiment

A sixth embodiment performs a blurring process similarly to the fifth embodiment, but the blurring process is performed on multiple pieces of position information detected by the trained model 30.

Figure 11:
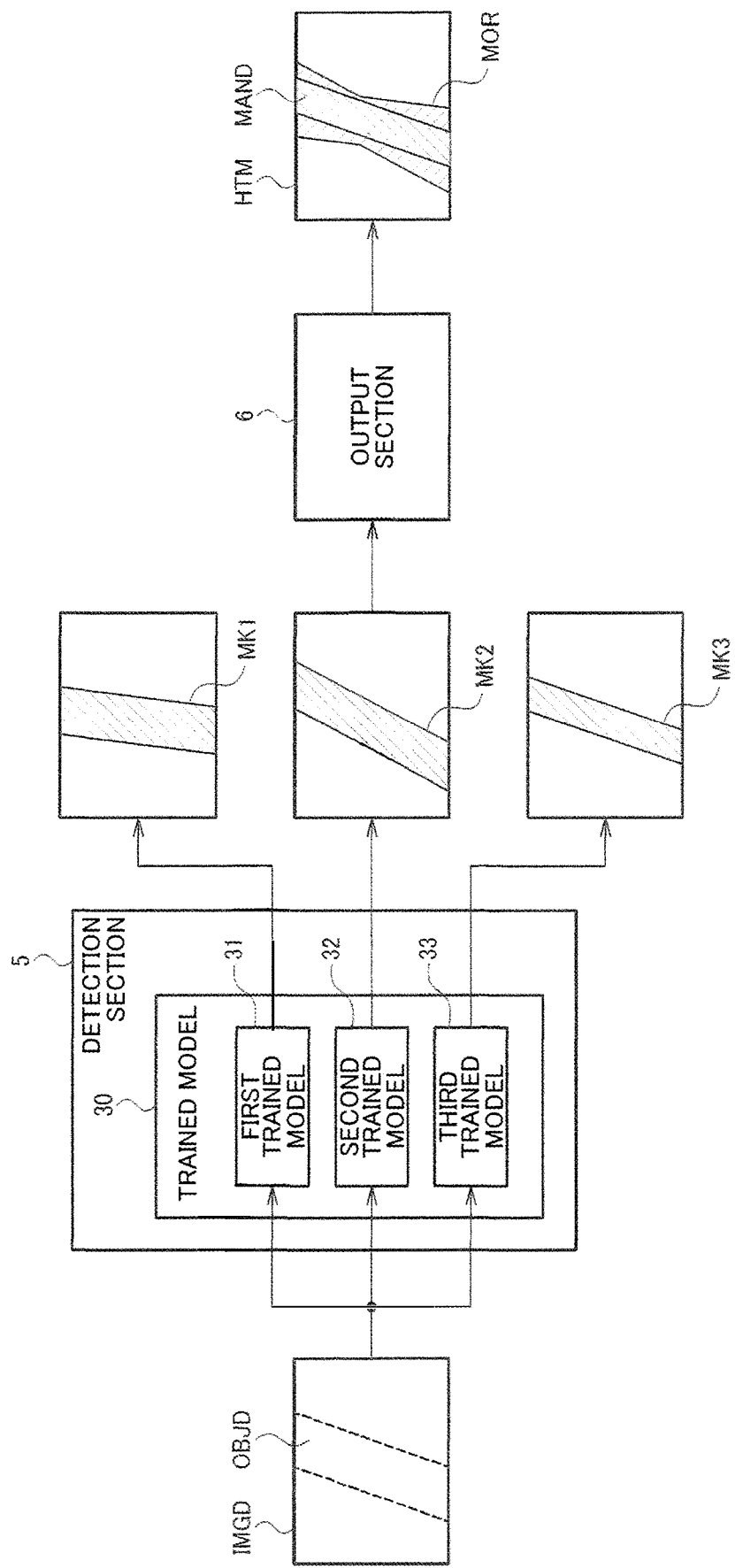
FIG. 11 illustrates a detection process and a display process in accordance with a sixth embodiment.

FIG. 11 illustrates a detection process and a display process in accordance with the sixth embodiment. Similarly, to the second embodiment, the trained model 30 includes the first trained model 31, the second trained model 32, and the third trained model 33. That is, the detection section 5 inputs the detection image IMGD to the trained models 31 to 33, and outputs the position information MK1 to MK 3 detected by the trained models 31 to 33, respectively.

The output section 6 performs the blurring process on the position information MK1 to MK3 to generate the position information HTM. While the blurring process may be performed in various manners, one example is described below.

The output section 6 obtains a logical AND and a logical OR of the position information MK1 to MK3. The training device 50 executes logical AND and logical OR operations with respect to each pixel in flag data, and outputs respective results of the logical AND and logical OR operations as flag data. A region corresponding to the logical AND of the position information MK1 to MK3 is defined as a region MAND, and a region corresponding to the logical OR of the position information MK1 to MK3 is defined as a region MOR. The output section 6 allocates a value of "1" to each pixel belonging to the region MAND, and performs the blurring process on the region MOR. The blurring process adds gradations to the region MOR. That is, in the region MOR, the training device 50 allocates a smaller value to a pixel farther from the region MAND.

Note that the blurring process is not limited to the one described above. For example, the output section 6 may perform the blurring process on each of the position information MK1 to MK3 to generate position information MK1" to MK3", and may generate the position information HTM using the position information MK1" to MK3". For example, the output section 6 may perform the blurring process on the region MOR in each of the position information MK1 to MK3 to generate the position information MK1" to MK3". Alternatively, the output section 6 may perform a blurring process to blur the boundary in each of the position information MK1 to MK3 to generate the position information MK1" to MK3". For example, the output section 6 may perform addition-averaging on the position information MK1" to MK3" to generate the position information HTM.

The present embodiment detects the position information MK1 to MK3 based on the trained models 31 to 33, respectively, then performs the blurring process on a region where the pieces of position information MK1 to MK3 do not overlap, and thereby generates the position information HTM of the object OBJD. By using this position information HTM, the present embodiment can display the position information in consideration of ambiguity of the boundary of the object OBJD. Note that the "region where the pieces of position information MK1 to MK3 do not overlap" means a region where at least one of the pieces of position information MK1 to MK3 does not overlap with the rest, and corresponds to a region excluding the region MAND from the region MOR.

8. Seventh Embodiment

A seventh embodiment performs training on each of a logical AND and a logical OR obtained from multiple annotations to enable detection and display of position information corresponding to the logical AND and position information corresponding to the logical OR.

Figure 12:
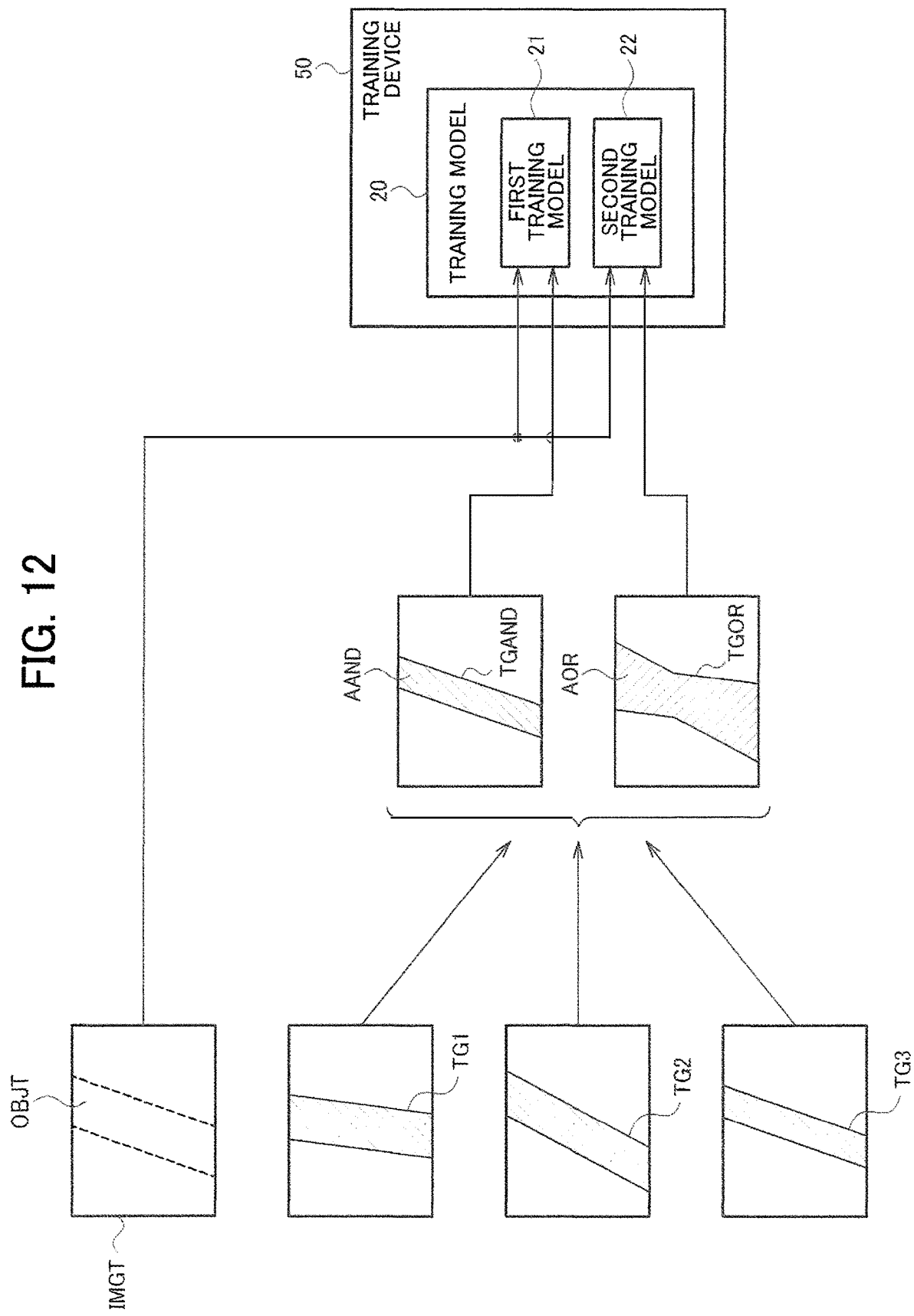
FIG. 12 illustrates a training process in accordance with a seventh embodiment.

FIG. 12 illustrates a training process in accordance with the seventh embodiment. The training device 50 obtains flag data TGAND corresponding to the logical AND of the annotations TG1 to TG3, and also obtains flag data TGOR corresponding to the logical OR of the annotations TG1 to TG3. The region AAND corresponds to the logical AND of the annotations TG1 to TG3, and the flag data TGAND is data obtained by setting a flag to each pixel belonging to the region AAND. The region AOR corresponds to the logical OR of the annotations TG1 to TG3, and the flag data TGOR is data obtained by setting a flag to each pixel belonging to the region AOR.

The training model 20 includes the first training model 21 and the second training model 22. The training device 50 inputs the training image IMGT to the training model 21, compares the first position information about the object OBJT detected by the training model 21 with the flag data TGAND, and gives feedback based on an error thereof to the training model 21. In addition, the training device 50 inputs the training image IMGT to the training model 22, compares the second position information about the object OBJT detected by the training model 22 with the flag data TGOR, and gives feedback based on an error thereof to the training model 22.

The training model 21 uses, for example, an inference algorithm for performing region detection (semantic segmentation). The training model 22 uses, for example, an inference algorithm for performing presence detection (detection). The training model 22 that performs the presence detection detects, for example, a rectangle that encompasses the object as position information. Note that inference algorithms used by the training models 21 and 22 are not limited thereto. For example, both of the training models 21 and 22 may perform the region detection. In this case, a rectangle that encompasses a region detected by the training model 22 may serve as the position information.

Figure 13:
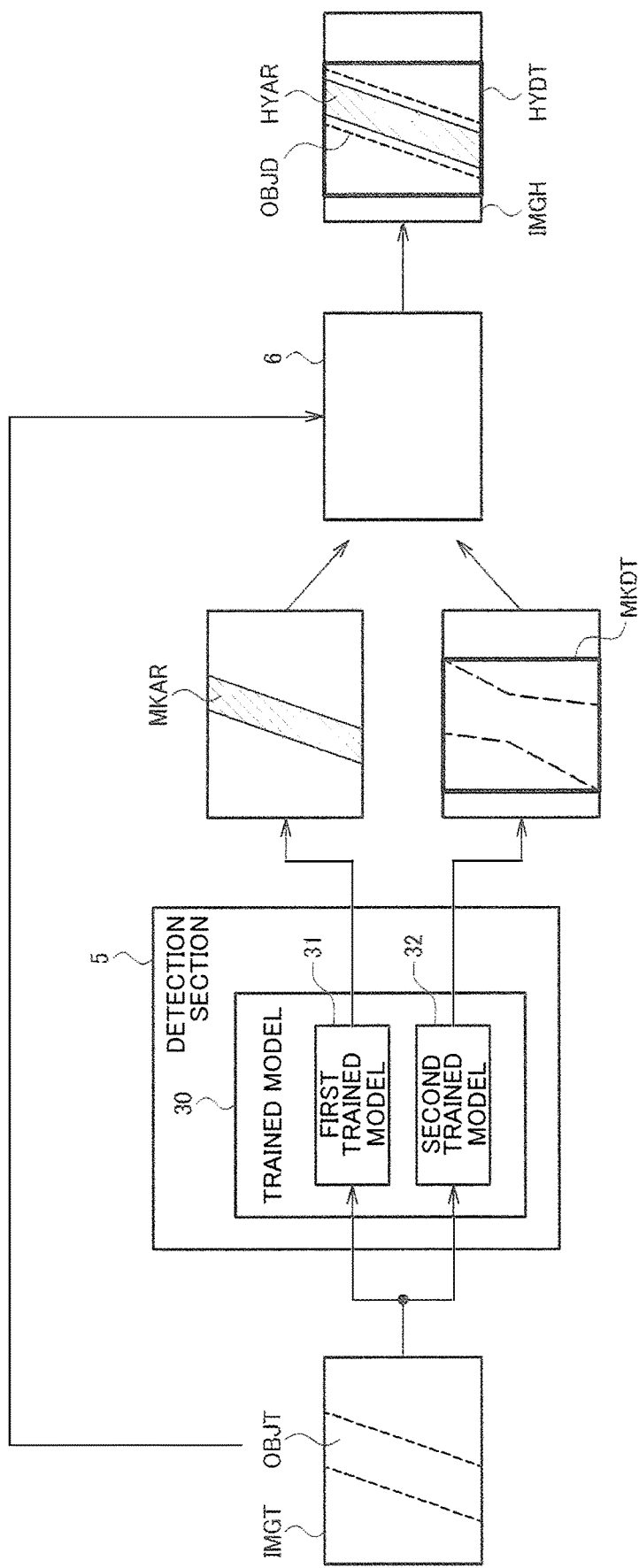
FIG. 13 illustrates a detection process and a display process in accordance with a seventh embodiment.

FIG. 13 illustrates a detection process and a display process in accordance with the seventh embodiment. The trained model 30 includes the first trained model 31 and the second trained model 32. The trained models 31 and 32 correspond to the training models 21 and 22 after the training, respectively.

The detection section 5 inputs the detection image IMGD to the trained model 31, and outputs first position information MKAR detected by the trained model 31. The position information MKAR is flag data in which a flag is added to a pixel belonging to a region where the object OBJD is detected. In addition, the detection section 5 inputs the detection image IMGD to the trained model 32, and outputs second position information MKDT detected by the trained model 32. The position information MKDT corresponds to a rectangle that encompasses a logical OR region indicated by dotted lines. However, in a case where the trained model 32 performs the presence detection, the logical OR region is not detected, and the position information MKDT corresponding to the rectangle is directly detected.

The output section 6 generates first display information HYAR based on the position information MKAR and second display information HYDT based on the position information MKDT. The output section 6 then combines the display information HYAR and HYDT with the detection image IMGD, with the display information HYAR and HYDT being distinguishable from each other, and thereby generates the display image IMGH. For example, the display information HYAR is information for adding a specific color to a region indicated by the position information MKAR. The display information HYDT is information for displaying the rectangle indicated by the position information MKDT.

The present embodiment can display the position information in consideration of ambiguity of the boundary of the object OBJD. Specifically, it is possible to generate the position information MKAR corresponding to an overlapping region of the annotations TG1 to TG3 and the position information MKDT corresponding to a non-overlapping region of the annotations TG1 to TG3. Using the position information MKAR and MKDT enables display in accordance with a probability of the position of the object OBJD. That is, a region having a higher probability of the position can be indicated by the display information HYAR, and a region where the presence of the object OBJD is likely but the probability is relatively low can be indicated by the display information HYDT.

9. Annotation and Object

Examples of annotation to a training image and examples of an object to be annotated will be described. While a description will be given of an example of cholecystectomy through laparoscopy, the application of the embodiments described above is not limited to the cholecystectomy through laparoscopy. That is, the present embodiments described above can be applied to a case of performing machine learning based on training data in which multiple annotations are added to an identical object in an identical image and detecting an object from an image based on the trained model.

FIG. 14 illustrates an example of annotation. A pre-annotation training image contains captured images of a liver KZ, a gallbladder TNN, and treatment tools TL1, TL2. This training image includes, within its angle of view, the common bile duct, the cystic duct, the Rouviere's sulcus, and the inferior border of the S4. In FIG. 14, a solid-line portion at the right lobe of the liver represents the origin of the Rouviere's sulcus (a relatively clear portion), and a dot-line portion represents gradual disappearance of the sulcus toward its end. Furthermore, a dot-line around the inferior border inside the left lobe of the liver represents a region of the inferior border of the S4, which is the object that can be visually recognized in the image but has an ambiguous boundary.

An operator who performs annotation identifies and tags each of the common bile duct, the cystic duct, the Rouviere's sulcus and the inferior border of the S4 in the training image. A post-annotation training image is provided with a tag TGA indicating the common bile duct, a tag TGB indicating the cystic duct, and a tag TGC indicating the Rouviere's sulcus, and a tag TGD indicating the inferior border of the S4. For example, the operator uses a pointing device such as a mouse or a touch panel to designate regions of the common bile duct and the like. The training device tags the regions designated by the operator on the training image.

The common bile duct and the cystic duct are examples of the object covered with organs or tissues. Even when such an object is present within the angle of view of a camera, the object itself is invisible in the image. Thus, the position and shape of the object are not clear. In an endoscopic image for cholecystectomy through laparoscopy, the common bile duct is covered with the liver and is not visibly displayed in the image. The Rouviere's sulcus and the inferior border of the S4 are examples of an object that is exposed visibly in the image but has an ambiguous boundary. In the endoscopic image for cholecystectomy through laparoscopy, the Rouviere's sulcus can be visually recognized and the origin of the sulcus is relatively clear. However, since the sulcus gradually disappears toward its end, the boundary of the Rouviere's sulcus is ambiguous. The inferior border of the S4, which is the inferior border inside the left lobe of the liver, can be visually recognized but has an ambiguous boundary.

Figure 15:
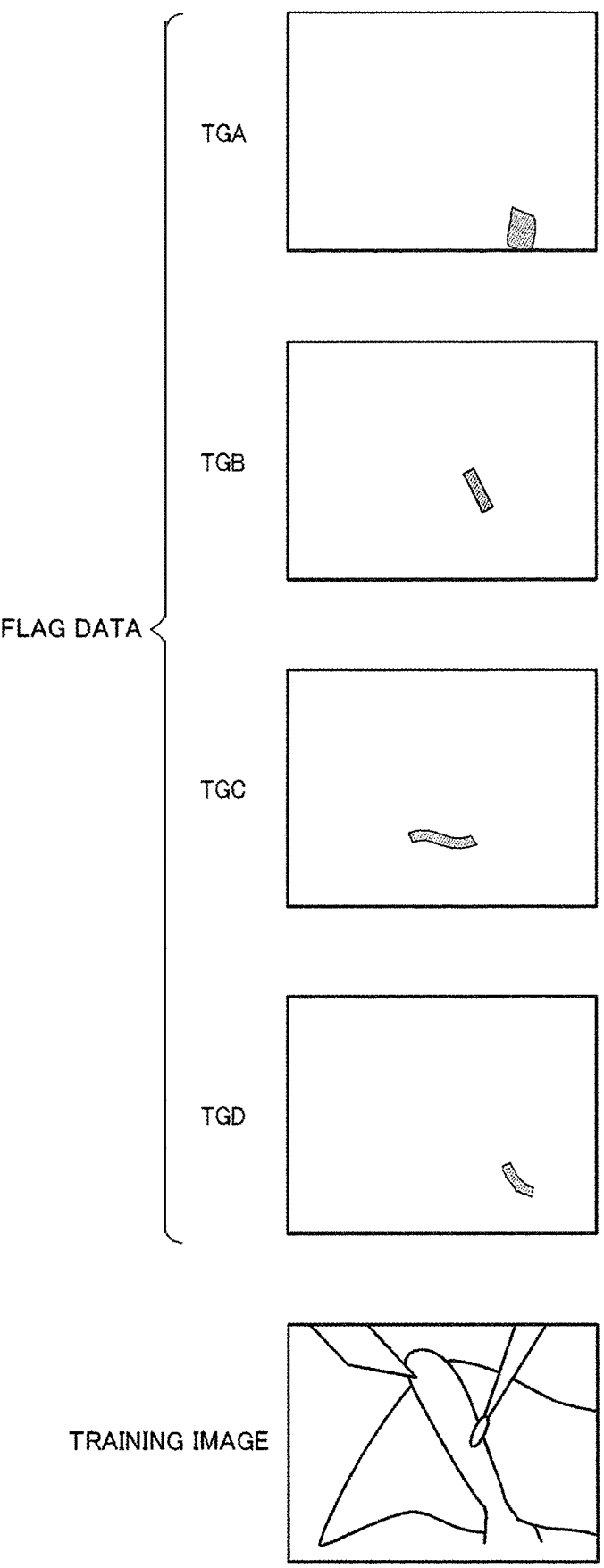
FIG. 15 illustrates an example of training data generated by the annotation.

FIG. 15 illustrates an example of training data generated by annotation. As illustrated in FIG. 15, a flag is set to each pixel in the tagged region. Map data in which a flag is set to each pixel is referred to as flag data. The flag data is generated for each of the tags TGA to TGD. That is, the training data is composed of the training image and four-layer flag data generated by tagging the training image.

Note that FIG. 15 illustrates annotations added by one operator. In a case where multiple operators make annotations, the number of sets of the four-layer flag data added to the identical training image amounts to the number of operators. That is, each of the common bile duct, the cystic duct, the Rouviere's sulcus and the inferior border of the S4 is annotated by as many times as the number of operators.

10. Training Device

Figure 16:
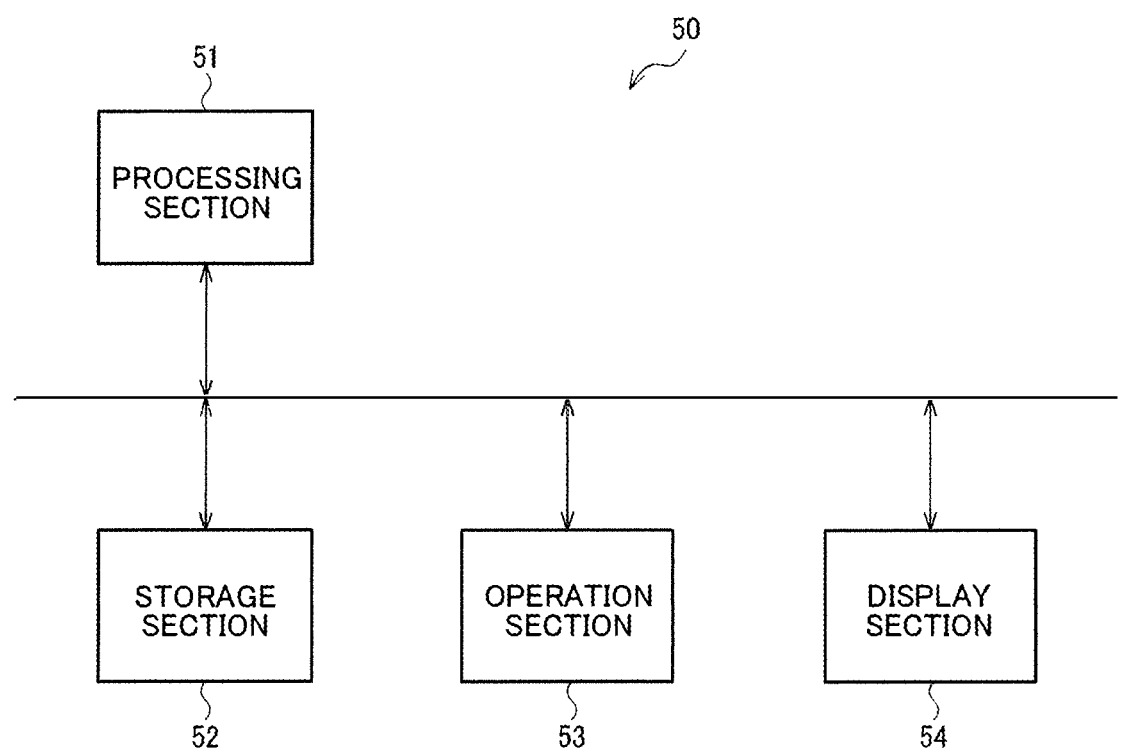
FIG. 16 illustrates a configuration example of a training device.

FIG. 16 is a configuration example of the training device 50. The training device 50 includes a processing section 51, a storage section 52, an operation section 53, and a display section 54. For example, the training device 50 is an information processing device such as a PC. The processing section 51 is a processor such as a CPU. The processing section 51 performs machine learning on a training model to generate a trained model. The storage section 52 includes a storage device such as a semiconductor memory or a hard disk drive. The operation section 53 is an operation input device of various types, such as a mouse, a touch panel, or a keyboard. The display section 54 is a display device such as a liquid crystal display. Note that the training device 50 may be a cloud system in which multiple information processing devices are connected via a network and perform parallel processing.

Note that the information processing system 10 illustrated in FIG. 1 may also function as the training device. In this case, the processing section 4, the storage section 7, the operation section 9, and the display section 3 correspond, respectively, to the processing section 51, the storage section 52, the operation section 53, and the display section 54 in the training device 50.

Figure 17:
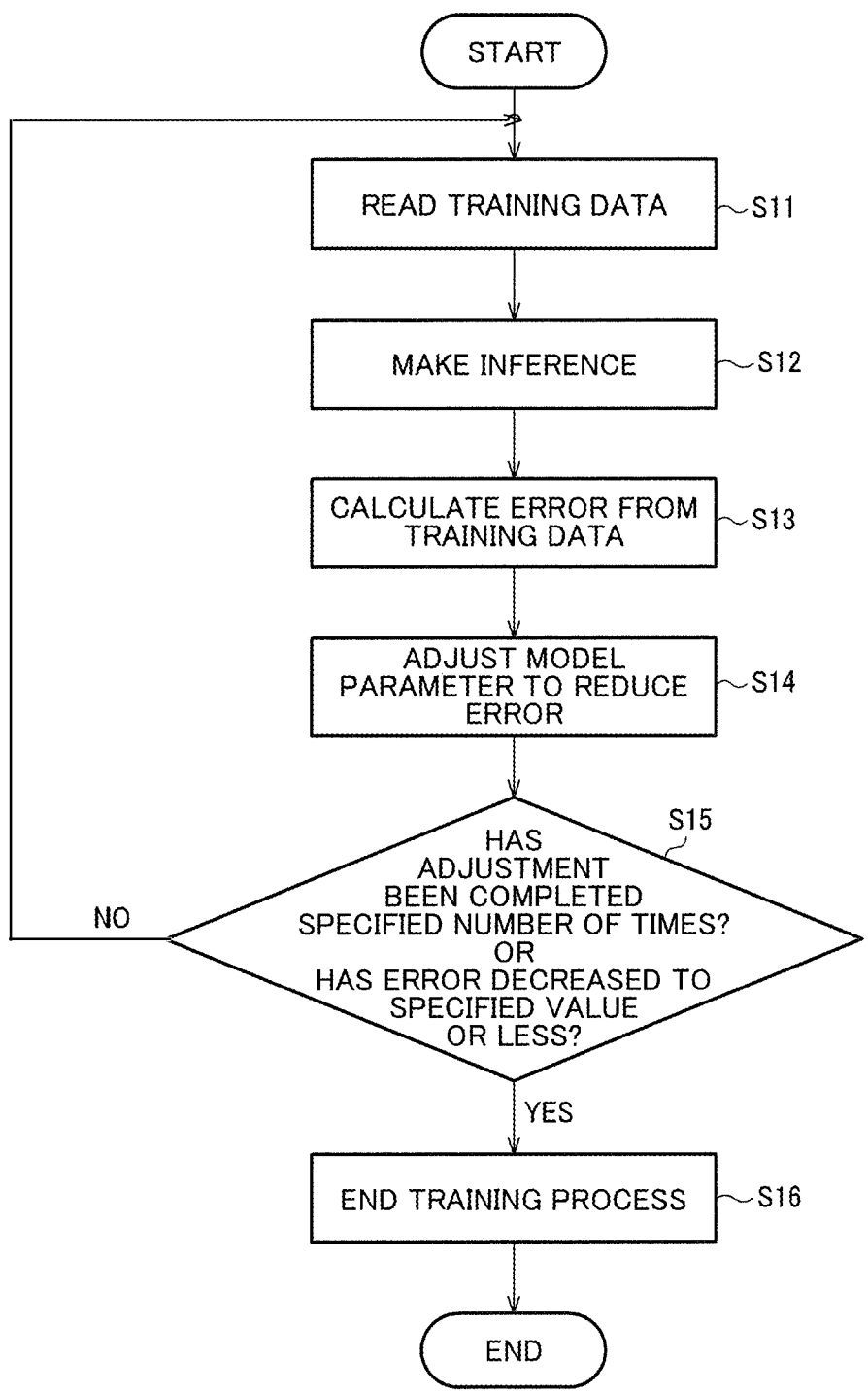
FIG. 17 is a flowchart describing a training procedure.

FIG. 17 is a flowchart describing a training procedure.

Training data is stored in the storage section 52. In step S11, the processing section 51 reads out the training data from the storage section 52. For example, for a single-time inference, the processing section 51 reads out one training image and corresponding flag data. Instead, multiple training images and corresponding flag data may be used for a single-time inference.

In step S12, the processing section 51 infers position information about an object, and outputs a result of the inference. That is, the processing section 51 inputs the training image to a neural network. The processing section 51 executes an inference process using the neural network, and outputs the position information about the object.

In step S13, the processing section 51 compares the position information inferred by the neural network with position information indicated by annotations in the training data, and calculates an error based on a result of the comparison.

In step S14, the processing section 51 adjusts a model parameter of the training model to reduce the error. That is, based on the error calculated in step S13, the processing section 51 adjusts a weight coefficient between nodes in the neural network or a like parameter.

In step S15, the processing section 51 determines whether the parameter adjustment has been completed a specified number of times. If the parameter adjustment has not been completed the specified number of times, the processing section 51 executes steps S11 to S15 again. If the parameter adjustment has been completed the specified number of times, the processing section 51 ends the training process as described in step S16. Alternatively, the processing section 51 determines whether the error calculated in step S13 has decreased to the specified value or less. If the error has not decreased to the specified value or less, the processing section 51 executes step S11 to S15 again. If the error has decreased to the specified value or less, the processing section 51 ends the training process as described in step S16. The training model after the training process is the trained model.

The training model and the trained model can include a neural network. The neural network includes an input layer that takes input data, an intermediate layer that performs arithmetic processing on the data input through the input layer, and an output layer that outputs data based on a result of the arithmetic processing output from the intermediate layer. In the present embodiments, the data input to the input layer is the training image or the detection image, and the data output from the output layer is the position information indicating the position and shape of the object. Note that the neural network may utilize various known artificial intelligence (AI) technologies. While use of the neural network requires development of software for execution of training or an inference algorithm, multiple software packages are currently available on the market or disclosed to the public for free, and the present embodiments can utilize such software packages. In addition, an algorithm for the machine learning in the neural network may be adopted from various known training algorithms. For example, a supervised training algorithm using backpropagation can be employed.

Furthermore, the trained model may be stored in an information storage medium, which is a computer-readable medium. The information storage medium can be implemented by an optical disk, a memory card, a hard disk drive (HDD), or a semiconductor memory, for example. The semiconductor memory is, for example, a read-only memory (ROM). The information processing system 10 illustrated in FIG. 1 performs various kinds of processing of the present embodiments based on a program and data stored in the information storage medium. That is, the information storage medium stores therein the program and parameter that cause a computer to execute the trained model of the present embodiments. The computer is a device including an input device, a processing section, a storage section, and an output section. The program is a program that causes the computer to execute the inference algorithm of the trained model. The parameter is a parameter used for the inference algorithm, and is, for example, a weight coefficient assigned between connected nodes in the neural network. The information storage medium may be any of various computer-readable storage media, for example, an optical disk such as a digital versatile disk (DVD) or a compact disk (CD), a magnetic optical disk, a hard disk, a memory such as a nonvolatile memory or a random-access memory (RAM), and the like.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An information processing system comprising:
 a storage device configured to store therein information of a trained model; and
 a processor configured to perform a detection process based on the information of the trained model and output position information detected in the detection process, the detection process being a process that detects the position information about an object from a detection image,
 wherein the trained model is trained based on training data in which an object in a training image is added with multiple annotations, and is trained to output position information about the object in the training image based on an overlapping relationship of the multiple annotations.

2. The information processing system as defined in claim 1,
wherein the trained model is trained to output the position information in the training image based on the overlapping relationship of the multiple annotations, the position information being information indicating a probability of the object in a continuous or stepwise manner, and
wherein, the processor
detects, in the detection process, the position information from the detection image, the position information being information indicating a probability of a position of the object in a continuous or stepwise manner, and
generates a display image by combining display information with the detection image based on the position information, the display information being information indicating the probability of the position of the object in a continuous or stepwise manner.

3. The information processing system as defined in claim 1,
wherein the trained model includes
a first trained model trained based on a region where the multiple annotations overlap, and
a second trained model trained based on a region where the multiple annotations do not overlap, and
wherein, in the detection process,
the processor
detects first position information about the object from the detection image based on the first trained model and second position information about the object from the detection image based on the second trained model, and
generates a display image by combining first display information based on the first position information and second display information based on the second position information with the detection image, with the first display information and the second display information being distinguishable from each other.

4. The information processing system as defined in claim 1,
wherein the trained model is trained based on the training data in which the overlapping relationship of the multiple annotations is weighted, and is trained to output the position information about the object in the training image based on the weighted overlapping relationship, and
wherein the processor
detects the position information from the detection image using the trained model trained based on the weighted overlapping relationship, the position information being information indicating a probability of a position of the object in a continuous or stepwise manner, and
generates a display image by combining display information with the detection image based on the position information, the display information being information indicating the probability of the position of the object in a continuous or stepwise manner.

5. The information processing system as defined in claim 1,
wherein the multiple annotations comprise first to n-th annotations, where n is an integer of two or greater,
wherein the trained model includes first to n-th trained models trained based on the first to n-th annotations, and
wherein the processor
detects, in the detection process, first to n-th position information about the object from the detection image based on the first to n-th trained models, and
generates display information by weighting an overlapping relationship of the first to n-th position information, the display information being information indicating a probability of a position of the object in a continuous or stepwise manner, and generates a display image by combining the display information with the detection image.

6. The information processing system as defined in claim 1,
wherein the trained model is trained based on the training data subjected to a blurring process on a region where the multiple annotations do not overlap, and
wherein the processor
detects the position information from the detection image using the trained model trained based on the training data subjected to the blurring process, the position information being information indicating a probability of a position of the object in a continuous or stepwise manner, and
generates a display image by combining display information with the detection image based on the position information, the display information being information indicating the probability of the position of the object in a continuous or stepwise manner.

7. The information processing system as defined in claim 1,
wherein the multiple annotations comprise first to n-th annotations, where n is an integer of two or greater,
wherein the trained model includes first to n-th trained models trained based on the first to n-th annotations, and
wherein the processor
detects, in the detection process, first to n-th position information about the object from the detection image based on the first to n-th trained models, and
performs a blurring process on a region where pieces of the first to n-th position information do not overlap, generates display information based on the position information after the blurring process, the display information being information indicating a probability of a position of the object in a continuous or stepwise manner, and generates a display image by combining the display information with the detection image.

8. The information processing system as defined in claim 1,
wherein the multiple annotations comprise first to n-th annotations, where n is an integer of two or greater,
wherein the trained model includes first to n-th trained models trained based on the first to n-th annotations, and is trained to output first to n-th position information about the object in the training image, and
wherein, in the detection process, the processor detects the first to n-th position information about the object from the detection image based on the first to n-th trained models, and outputs the position information about the object based on an overlapping relationship of the first to n-th position information.

9. An endoscope system comprising:
a processor unit including the information processing system according to claim 1;
an endoscopic scope connected to the processor unit, and configured to capture the detection image and transmit the detection image to the processor unit; and
a display device connected to the processor unit, and configured to display the detection image on which display information indicating a position of the object is superimposed, based on the position information about the object detected from the detection image by the information processing system.

10. A non-transitory information storage medium configured to store therein a trained model,
wherein the trained model causes a computer to perform a detection process of receiving an input of a detection image to a neural network and detecting an object, and to output position information detected by the detection process,
wherein the neural network comprises:
an input layer configured to take input data;
an intermediate layer configured to perform arithmetic processing on the data input through the input layer; and
an output layer configured to output data based on a result of the arithmetic processing output from the intermediate layer, and
wherein the trained model is trained based on training data in which an object in a training image is added with multiple annotations, and is trained to output position information about the object in the training image based on an overlapping relationship of the multiple annotations.

11. An information processing method of performing a detection process based on a trained model,
wherein the trained model is trained based on training data in which an object in a training image is added with multiple annotations, and is trained to output position information about the object in the training image based on an overlapping relationship of the multiple annotations, and
wherein the information processing method comprises:
performing the detection process of detecting position information about an object from a detection image; and
outputting the position information detected by the detection process.

* * * * *